US006709384B1

(12) United States Patent
Donnelly et al.

(10) Patent No.: US 6,709,384 B1
(45) Date of Patent: Mar. 23, 2004

(54) INFANT THERMAL SUPPORT DEVICE

(75) Inventors: Michael M. Donnelly, Cincinnati, OH (US); Francis Joseph Buchholz, III; Brent C. Jacobsen, both of Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 09/688,528

(22) Filed: Oct. 16, 2000

Related U.S. Application Data

(63) Continuation of application No. 09/419,527, filed on Oct. 18, 1999, now Pat. No. 6,270,452, which is a continuation of application No. 09/044,899, filed on Mar. 20, 1998, now Pat. No. 5,971,914, which is a continuation of application No. 08/497,384, filed on Jun. 30, 1995, now Pat. No. 5,817,002, which is a continuation of application No. 08/169,675, filed on Dec. 17, 1993, now Pat. No. 5,453,077.

(51) Int. Cl.$^7$ ............................................. A61G 11/00
(52) U.S. Cl. ....................................................... 600/22
(58) Field of Search ............................. 600/21–22; 5/97

(56) References Cited

U.S. PATENT DOCUMENTS

| | | |
|---|---|---|
| 3,069,700 A | 12/1962 | Berlin |
| 3,158,150 A | 11/1964 | Croasdaile |
| 3,335,713 A | 8/1967 | Grosholz et al. |

(List continued on next page.)

FOREIGN PATENT DOCUMENTS

| | | |
|---|---|---|
| DE | 2061704 | 7/1979 |
| DE | 3607575 | 9/1987 |
| EP | 0236851 | 2/1987 |
| FR | 2031559 | 11/1970 |
| GB | 1232048 | 5/1971 |
| GB | 2175213 | 11/1988 |
| JP | 122184 | 11/1974 |
| WO | 90/09771 | 9/1990 |

OTHER PUBLICATIONS

12/71 Journal of Pediatrics "Air Curtain Incubator for Use in a Intensive–Care Nursery", Musch, Adams and Sunshine, vol. 79, No. 6, pp. 1024–1030.
INFA–CARE 2000 brochure, Infa–Care, Inc., 1972.
"Incubator–Baby Side Shows", Silverman, *Pediatrics*, vol. 64, No. 2, pp. 124–135, Aug. 1979.
"Introducing the Isolette Servo–Controller", Air–Shields, Inc. Brochure, four pages, 1961.

(List continued on next page.)

*Primary Examiner*—John P. Lacyk
(74) *Attorney, Agent, or Firm*—Barnes & Thornburg

(57) ABSTRACT

An infant thermal support device which provides convective heat transfer similar to an incubator yet which allows for unlimited care provider access to the infant without compromising the infant's thermal environment. The device has an infant support with head and foot ends and lateral sides, and provides a heated curtain of air traveling over an infant on the support to maintain the temperature of the infant at an appropriate level. Vertically oriented curtains of air travel upwardly from the lateral edges and at least one end of the support. The device provides warmth to the infant on the support by virtue of the heated air curtain, and the vertically oriented air curtains reduced perturbations of the heated air curtain caused by physical disturbances adjacent to the device such that a canopy enclosing the device is not required. The device further comprises a raisable and lowerable canopy and infrared heater, such that the device can function as either an infant radiant warmer, an incubator or both. Sensors mounted on the device sense disturbances around the device and the position of the canopy and vary the speeds of the heated air curtain and perturbation reducing curtains accordingly.

29 Claims, 6 Drawing Sheets

U.S. PATENT DOCUMENTS

| | | |
|---|---|---|
| 3,387,600 A | 6/1968 | Terzian |
| 3,511,162 A | 5/1970 | Truhan |
| 3,618,734 A | 11/1971 | Khan |
| 3,776,217 A | 12/1973 | van Galen et al. |
| 3,782,362 A | 1/1974 | Puzio |
| 3,789,853 A | 2/1974 | Reinhard |
| 3,821,947 A | 7/1974 | Schossow |
| 3,858,570 A | 1/1975 | Beld et al. |
| 4,034,740 A | 7/1977 | Atherton et al. |
| 4,063,495 A | 12/1977 | Duvlis |
| 4,140,105 A | 2/1979 | Duvlis |
| 4,161,172 A | 7/1979 | Pickering |
| 4,321,913 A | 3/1982 | Maluta et al. |
| 4,361,137 A | 11/1982 | Grosholz |
| 4,423,669 A | 1/1984 | Bullock et al. |
| 4,617,912 A | 10/1986 | Beer et al. |
| 4,750,474 A | 6/1988 | Dukhan et al. |
| 4,809,677 A | 3/1989 | Mackin et al. |
| 4,846,783 A | 7/1989 | Koch et al. |
| 4,885,918 A | 12/1989 | Vaccaro |
| 4,936,824 A | 6/1990 | Koch et al. |
| 5,119,467 A | 6/1992 | Barsky et al. |
| 5,162,038 A | 11/1992 | Wilker |
| 5,224,923 A | 7/1993 | Moffett et al. |
| 5,242,375 A | 9/1993 | McDonough |
| 5,285,054 A | 2/1994 | Barsky |
| 5,285,519 A | 2/1994 | Barsky et al. |
| 5,308,310 A | 5/1994 | Roff et al. |
| 5,316,542 A | 5/1994 | Koch et al. |
| 5,330,415 A | 7/1994 | Storti et al. |
| 5,336,156 A | 8/1994 | Miller et al. |
| 5,352,869 A | 10/1994 | Barsky |
| 5,453,077 A | 9/1995 | Donnelly et al. |
| 5,498,229 A | 3/1996 | Barsky et al. |
| 5,649,896 A | 7/1997 | Barsky |
| 6,049,929 A | 4/2000 | Prows et al. |
| 6,071,228 A | 6/2000 | Speraw et al. |

OTHER PUBLICATIONS

Medical Intelligence, Current Concepts, "Temperature Regulation in the Newborn Infant", SIlverman and Sinclair, *New England Journal of Medicine* 274:92–94, 146–146, Jan. 1996.

"Effect of Maintenance of 'Normal' Temperature on Survival of Infants in Low Birth Weight", Buetow and Klein, *Pediatrics*, vol. 34, pp. 163–170, Aug. 1964.

"The Control of body Temperature in the Small Newborn Infant by Low–Energy Infra–Red Radiation", Agate and Silverman, *Pediatrics*, vol. 21, pp. 725–733, May 1963.

"Body Temperature and Survival of Premature Infants", Day, Caliguiri, Kamenski, and Ehrlich, *Pediatrics*, vol. 34, pp. 171–181, Aug. 1964.

"Future Directions for Device Design and Infant Management", Perlstein, *Medical Instrumentation*, vol. 21, No. 1, pp. 36–41, Feb. 1987.

"A Sequential Trial of the Nonthermal Effect of Atmospheric Humidity on Survival of Newborn Infants of Low Birth Weight", Silverman, Agate, and Fertig, *Pediatrics*, vol. 31, No. 5, pp. 719–724, May 1963.

"The Effect of Humidity on Survival of Newly Born Premature Infants", Silverman and Blanc, *Pediatrics*, vol. 20, No. 3, pp. 477–487, Sep. 1957.

"The Influence of the Thermal Environmant Upon the Survival of Newly Born Premature Infants", Silverman, Fertig, and Berger, *Pediatrics*, pp. 876–884, Nov. 1958.

"Regulation of Body Temperature in Pediatric Surgery", Silverman, Sinclair, and Scopes, *Journal of Pediatric Surgery*, vol. 1, No. 4, pp. 321–328, Aug. 1966.

INFANT THERMAL SUPPORT DEVICE

This is a continuation application of application Ser. No. 09/419,527, filed Oct. 18, 1999, U.S. Pat. No. 6,270,452 which is a continuation application of application Ser. No. 09/044,899, filed Mar. 20, 1998, now U.S. Pat. No. 5,971,914, which is a continuation application of application Ser. No. 08/497,384, filed Jun. 30, 1995, now U.S. Pat. No. 5,817,002, which is a continuation application of application Ser. No. 08/169,675, filed Dec. 17, 1993, now U.S. Pat. No. 5,453,077.

FIELD OF THE INVENTION

This invention relates generally to neonatal patient treatment devices, and more particularly to a thermal support device for maintaining appropriate temperature of an infant.

BACKGROUND OF THE INVENTION

Incubators and radiant warmers have both been used to maintain the appropriate body temperature of small or premature infants. An incubator provides an enclosure, generally transparent, within which heated air is circulated to minimize heat loss of the infant. Heat is transferred to the infant via convective heat transfer. A major drawback of the typical incubator is that it provides for only limited access by a care provider to the infant. More particularly, the incubator typically provides a large access door for placing the infant into or removing the infant from the incubator. However, it will be appreciated that opening such a door causes rapid cooling of the interior of the infant, and therefore should be opened as seldom as possible in order to maintain the appropriate temperature of the incubator interior and hence the infant. Thus, most incubators are provided with means of supplemental access in the form of hand ports or small entry doors for routine care of the infant to minimize heat loss during care of the infant. Such small entry doors and hand ports, however, are quite limiting in that a care provider does not have complete access to and mobility with respect to an infant within the incubator.

Radiant warmers, on the other hand, provide for continuous and open access to an infant to accommodate a high frequency of care provider intervention. In radiant warmers heat is transferred to the infant via radiative heat transfer. Radiant warmers typically include infrared heaters which emit infrared energy which is absorbed by the skin of the infant. The infrared heater is typically mounted to a support which is suspended above the infant support surface of the radiant warmer. There is no canopy or enclosure as in incubators. Radiant warmers thus provide open access to infants requiring surgery, for example, or other procedures requiring multiple care providers to have access to an unobstructed sight of the infant. However, while incubators are typically provided with humidification mechanisms to raise the level of relative humidity within the incubator, thus contributing to a reduction in heat loss from evaporation of fluids from the infant, radiant warmers due to their open nature and the mode of heat transfer employed cause infant evaporative water losses which are significantly greater than those encountered by an infant within an incubator. Another disadvantage of the radiant warmer, when compared to an incubator, is that the infant is directly exposed to ambient nursery contaminants in the form of noise and unfiltered air. The incubator, on the other hand, being an enclosure for the infant, reduces the effects of nursery environmental conditions on the infant.

SUMMARY OF THE INVENTION

It has therefore been an objective of the present invention to improve upon prior art incubators by providing an incubator which will maintain the appropriate temperature of a premature infant via convective heat transfer yet which will also increase caregiver access to the infant.

It has been another objective of the present invention to combine the advantages of each of the prior art types of incubators and radiant warmers into a single infant warming device, which combination exploits the advantages of each of these two types of prior art devices but as well avoids the inherent disadvantages in them when employed singly.

In accordance with the objectives of the present invention and a preferred embodiment thereof, the present invention comprises, in its broadest form, an infant thermal support device providing convective heat transfer to the infant similar to an incubator, yet which allows for unlimited care provider access to an infant, and without compromising the infant's thermal environment. The invention provides an infant support having head and foot ends and lateral sides, with the support providing a heated curtain of air traveling over an infant on the support to maintain the temperature of the infant's skin at an appropriate level. The support provides curtains of air traveling upwardly from the lateral sides and at least one of the ends of the support. The warming device provides warmth to the infant on the support by virtue of the heated air curtain, and the upwardly oriented air curtains reduce perturbations of the heated air curtain caused by physical disturbances adjacent the device such that the device does not require a canopy enclosing the device to maintain the infant warm. Thus, the device provides unlimited caregiver access to an infant supported on the support, while maintaining the appropriate temperature of the infant by a convective mode of heat transfer.

The device in its preferred form provides three infant thermal environment controlling air curtains, and at least three air curtains protecting the three thermal environment air curtains from perturbations due to physical disturbances adjacent to the device. The first heated air curtain travels from the foot end of the infant support toward the head end of the infant support over an infant supported by the support, at a velocity of up to approximately 0.1 meters per second and temperature of up to about 38–39° C. The second and third heated air curtains travel from the lateral edges of the support upwardly and toward one another at approximately 45° angles relative to the support and over the infant supported by the support, at a velocity of up to approximately 0.5 meters per second and temperature of up to approximately 38–39° C.

The three air curtains which prevent perturbations of the heated air curtains from physical disturbances travel upwardly preferably vertically from the lateral sides and the foot end of the support at a velocity of approximately 1–2 meters per second.

The infant warming device further preferably comprises a canopy mounted over the infant support and adapted to be raised and lowered relative to the support, such that the canopy can be lowered to a lowermost position which substantially encloses the support. The device can then function, with canopy lowered, as a traditional enclosed incubator. With the canopy raised to provide complete and unrestricted access to the infant, the three heated air curtains and three perturbation-reducing air curtains maintain the infant thermal environment.

The device of the present invention further preferably provides an infrared heater mounted above the support and which is adapted to be raised and lowered relative to the support along with the canopy. The device, in this form, is in essence a combination infant radiant warmer and incubator. Thus, the device can function as either a traditional incubator, a traditional radiant warmer, or can function simultaneously as both, with the raisable and lowerable canopy, heated air curtains and perturbation-reducing air curtains and infrared heater maintaining the thermal environment of the infant as desired.

Another feature of the present invention is a heated shelf storage area on the infant support portion of the warmer for storing various items such as probes, probe covers and laryngoscopes.

Yet another feature of the present invention is the provision of a canopy including a light reduction medium for selected darkening of the infant sleep area of the warmer.

A further feature of the present invention is the provision of a motion sensor mounted on the infant support for sensing disturbances around the infant thermal support device, and a controller for controlling the speed of the fan which provides the curtains of air traveling upwardly. The controller, upon the sensor sensing a disturbance, is operable to increase the speed of the fan providing those curtains of air traveling upwardly to further reduce perturbations of the heated air curtain or curtains.

Still a further feature of the present invention is the provision of a position sensor associated with the raisable and lowerable canopy for determining the relative position of the canopy relative to the infant support, and a controller which, upon the sensor sensing the relative position of the canopy with respect to the support, is operable to decrease the speed of the fan providing the upwardly traveling air curtains as the need for those upwardly traveling air curtains diminishes as the canopy is lowered and approaches the infant support, and to decrease the speed of the fan providing the heated air curtains as the need for the heated air curtains diminishes due to the infant becoming substantially enclosed by the support and canopy.

The present invention provides numerous advantages over traditional incubators and radiant warmers, one of which is that the device provides an infant thermal environment very nearly identical to that provided by a traditional incubator, yet which provides totally unrestricted and unlimited access to the infant by a care provider, unlike traditional incubators.

Another advantage of the present invention is that it combines the benefits of both traditional incubators and radiant warmers into a single device, thus exploiting the advantages of both while tending to eliminate the disadvantages when employing either singly.

These and other objects and advantages of the present invention will become more readily apparent during the following detailed description taken in conjunction with the drawings herein, in which:

DETAILED DESCRIPTION OF THE INVENTION

Figure 1:
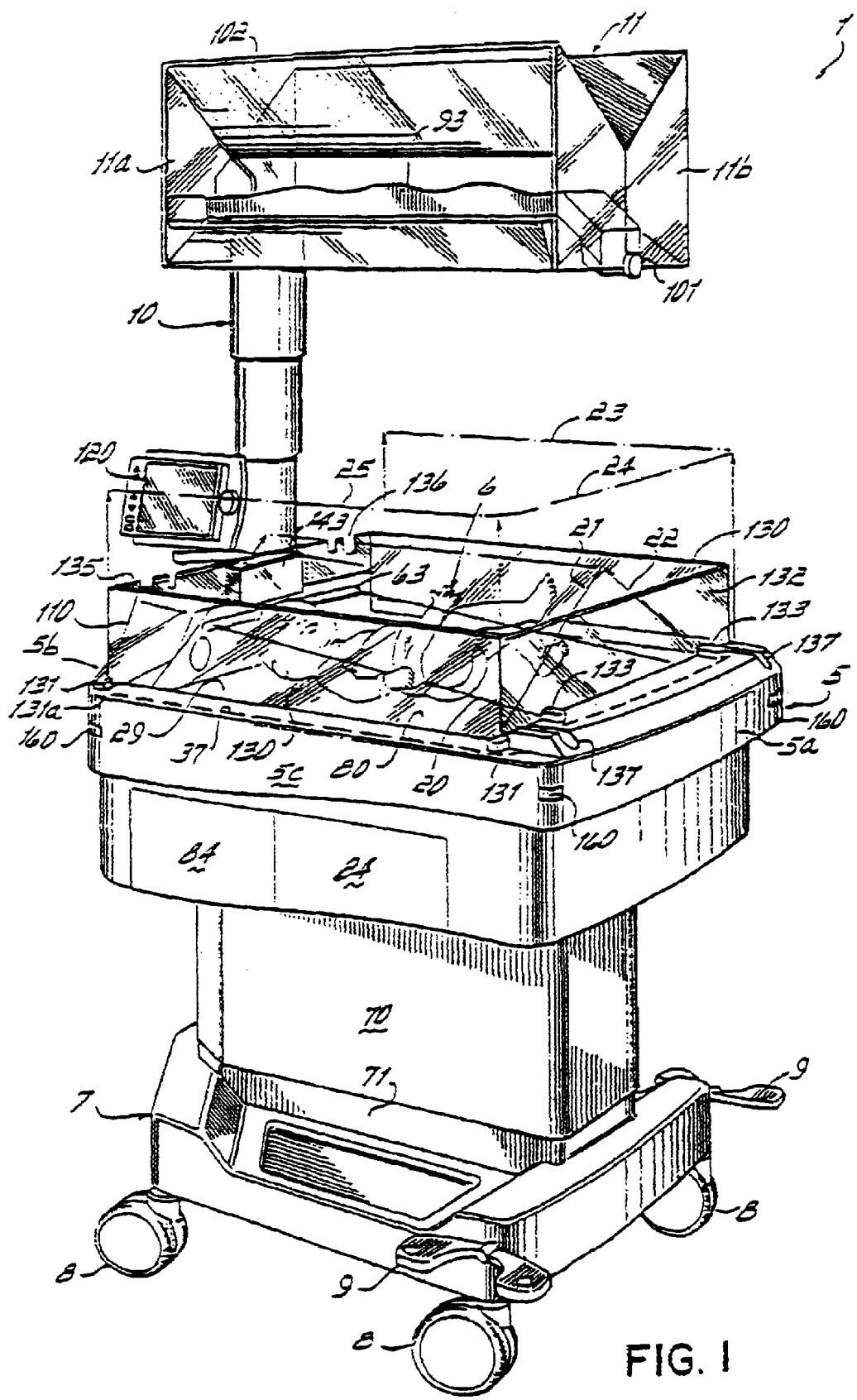
FIG. 1 is a perspective view of the infant warming device of the present invention.

With reference first to FIG. 1, there is illustrated the infant warming device 1 of the present invention. The device 1 includes, generally, an infant supporting portion 5 for supporting an infant 6, a base portion 7 having castors 8 and brake/steer pedals 9, and a canopy support arm 10 supporting a canopy 11.

Figure 2:
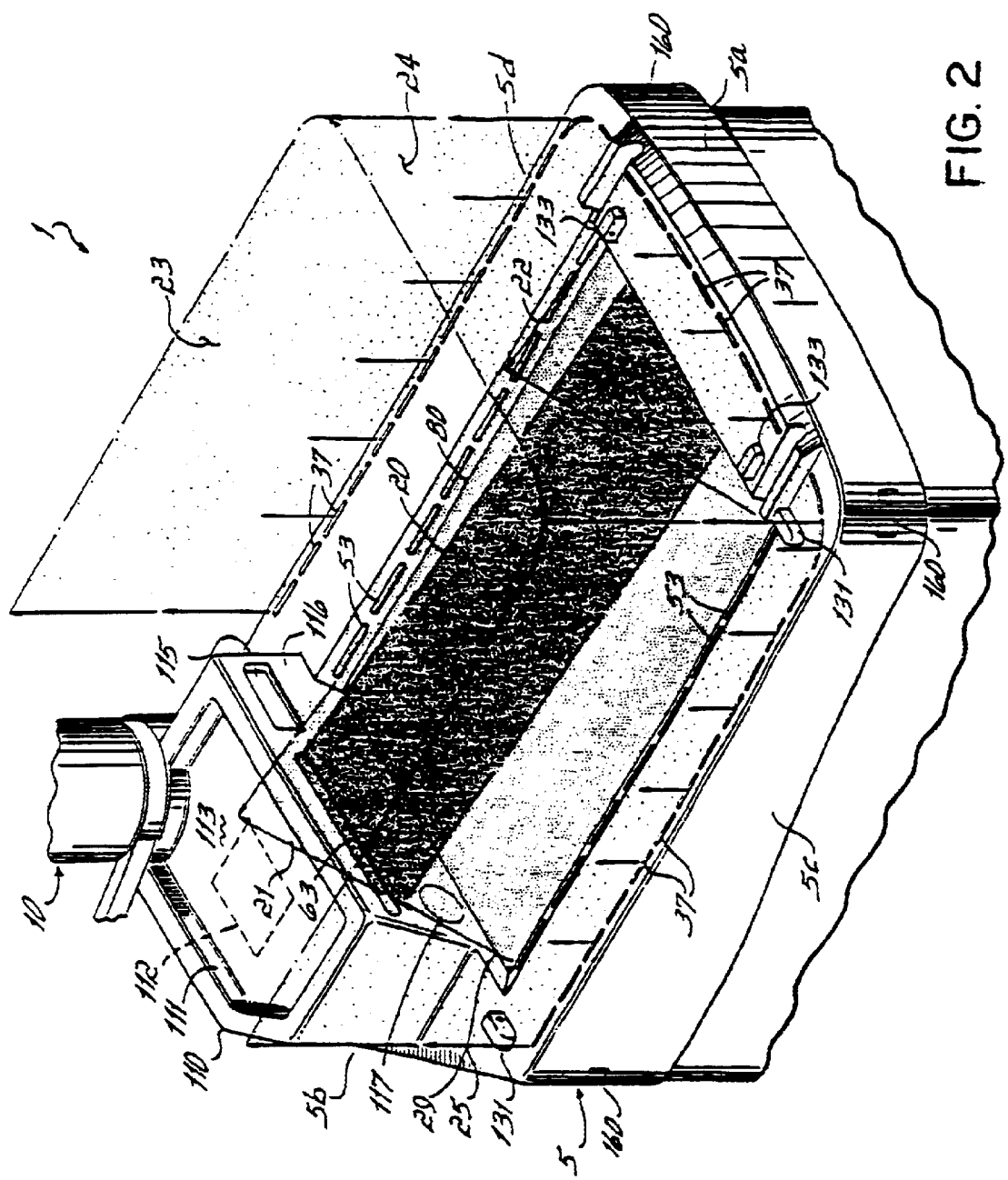
FIG. 2 is an enlarged perspective view of the air curtain scheme of the present invention.
Figure 3:
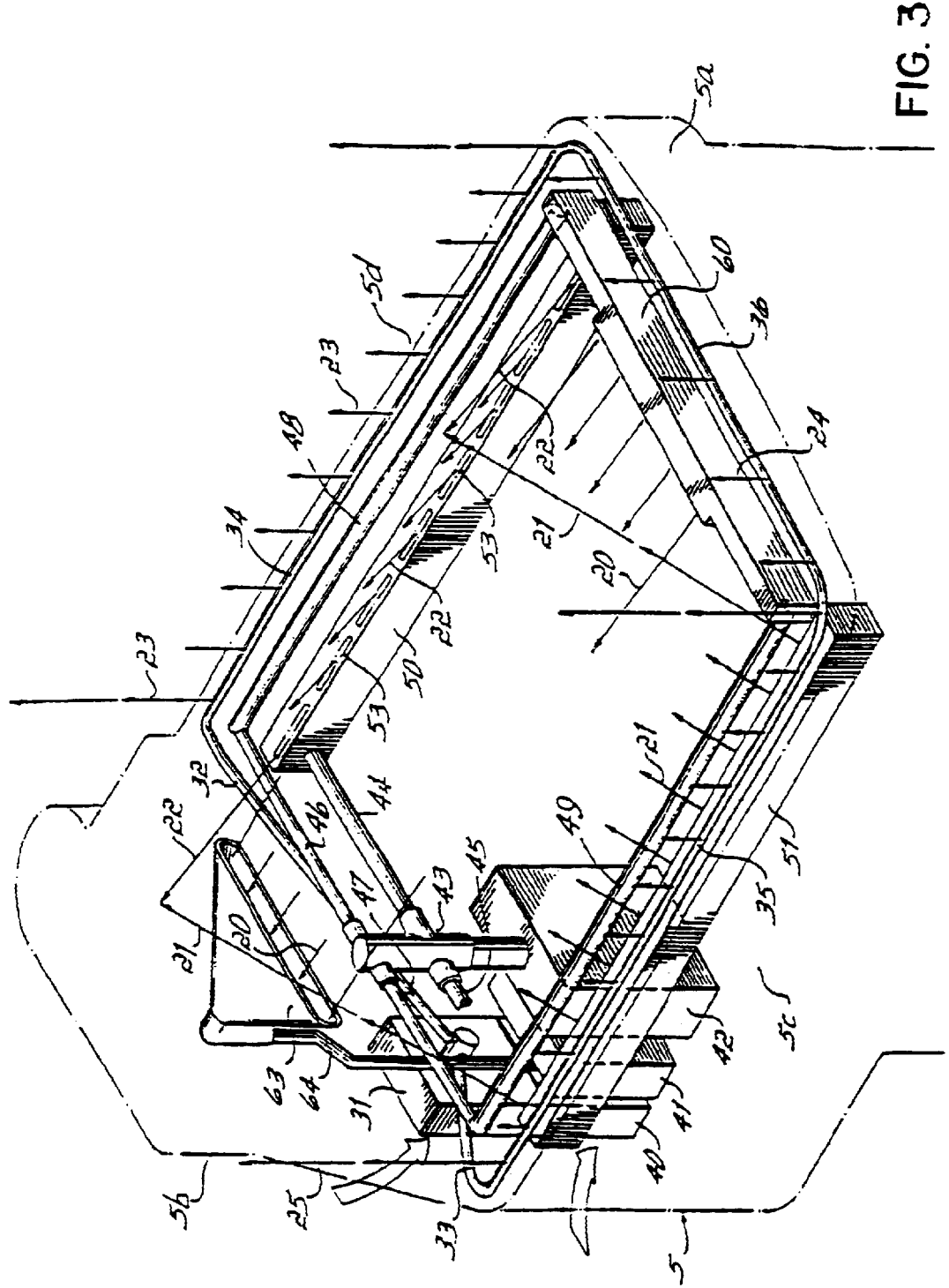
FIG. 3 is a view similar to FIG. 2 but illustrating the pneumatic circuitry for providing the air curtain scheme.

Referring to FIGS. 1 and 2, the infant warming device 1 of the present invention, in its preferred form, provides three heated air curtains 20, 21 and 22, and three additional air curtains 23, 24 and 25. More particularly, heated air curtain 20 travels from the foot end 5a towards the head end 5b of infant support 5 and over an infant 6 supported thereby closely adjacent the infant. Air curtains 21 and 22 travel upwardly from lateral sides 5c and 5d of patient support 5 upwardly toward one another and over the infant 6 supported by the support. The curtains 21 and 22 each preferably form an angle of approximately 45° with respect to the supporting surface 29 of the infant support 5. Supporting surface 29 defines an infant platform area approximately 26.25 inches long and 17.5 inches wide. Air curtain 20 preferably has a velocity of up to approximately 0.1 meters per second and a temperature of up to approximately 38–39° C., while air curtains 21 and 22 each preferably have a velocity of up to approximately 0.5 meters per second and a temperature of up to approximately 38–39° C. Air curtains 23, 24 and 25 have a velocity of approximately 1–2 meters per second and preferably are oriented generally vertically.

Referring to FIGS. 1–5, and describing the air flow system of the infant warming device 1 of the present invention in more detail, at the lower head end 5b of the patient support portion 5 of the device 1 there is an intake or grill 30 for drawing in ambient air from the surroundings. A fan 31 supplies air to conduits or passages 32 and 33 which connect with passages 34, 35 and 36 in the lateral sides 5c, 5d and foot end 5a, respectively, of the patient support 5. Slots 37 allow air to escape from the passages 34, 35 and 36, and thus forming the vertical, upwardly traveling air curtains 23, 24 and 25. Slots 37 are approximately 2 inches long and 0.062 inches wide.

Another fan 40 likewise receives ambient air from air intake or grill 30 and supplies it to a filter 41. The filtered air then passes through a humidifier 42 and on into a manifold 43 which channels air through two sets of conduits or passages, 44, 45 and 46, 47. Conduits or passages 44, 45 channel air to rectangular passageways 50, 51 respectively, within the lateral sides 5d, 5c respectively of support portion 5 of the device 1. The air passing through passageways 50, 51 is heated by heaters 52 on the floor of each passageway, and exits slots 53 thus forming air curtains 21 and 22. It will be appreciated though that heaters 52 could be positioned at locations other than the floor of the passageway. Slots 53 are approximately 3 inches long, 0.375 inches wide and 2 inches deep. The approximate distance between the slots 53 across the lateral dimension of the support 5 is approximately 18 inches. Air curtains 21 and 22 converge above patient support surface 29 at an approximate distance ranging from 9 to 14 inches.

Conduits or passages 46 and 47 supply a rectangular, though other cross-sections may be employed, passageway 60 in the foot end 5a of the support portion 5 of the device 1. Air passing through passageway 60 is heated by heater 61

(FIG. 4) on the floor of that passageway, though other locations for heater 61 may be employed. The heated air exits slots 62 and travels from the foot end 5a to the head end 5b and enters intake 63 in the head end 5b of the support 5. Return air is channeled through conduit 64 downwardly and back into the air circuit upstream of filter 41. Slots 62 are generally the same dimensions as slots 53; slots 62 are located approximately in the same horizontal plane as slots 53. Intake 63 is approximately 0.5 inches wide and 9 inches long, and is located approximately 2.75 inches above the horizontal plane of slots 53 and 62.

Figure 4:
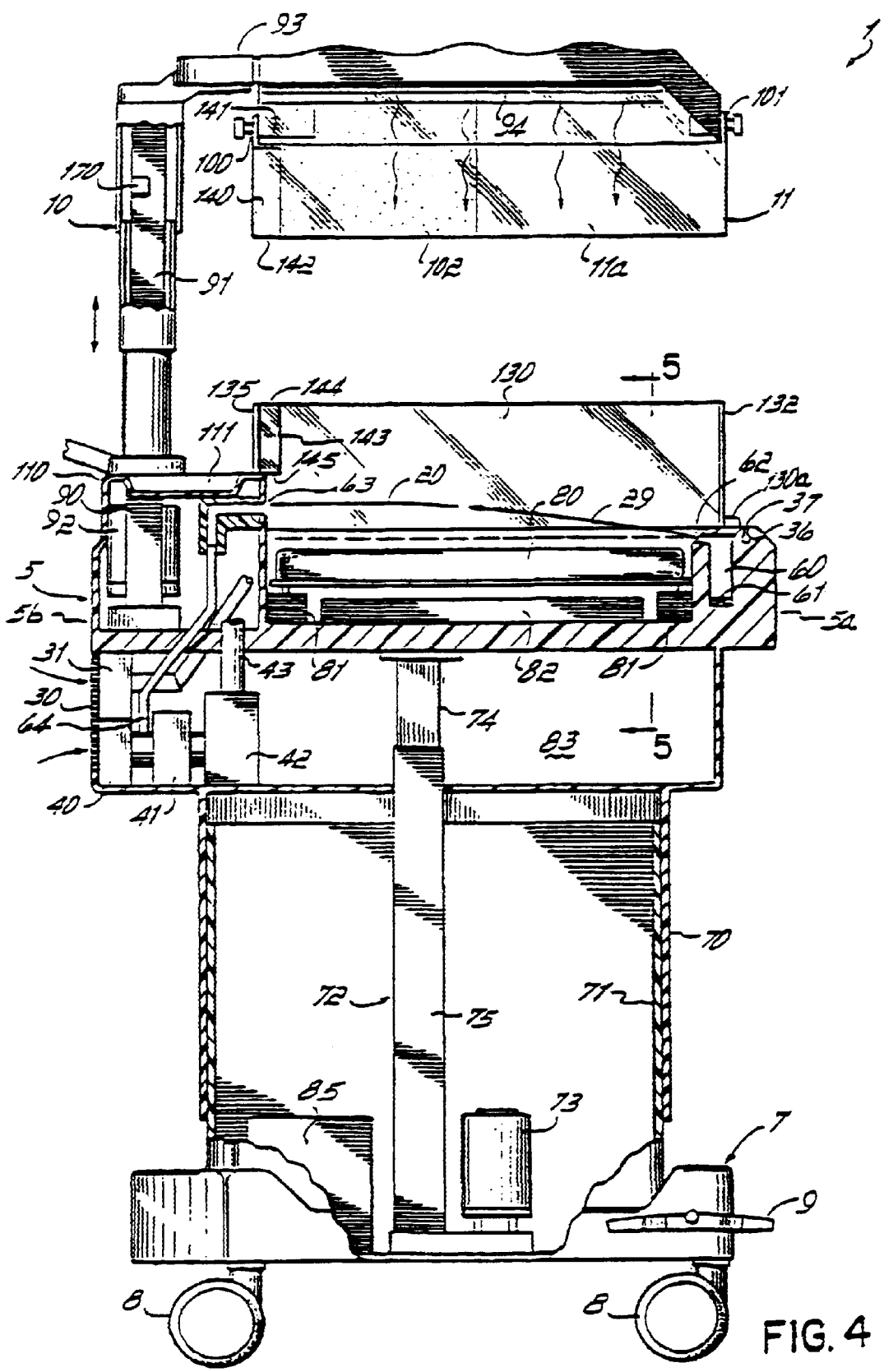
FIG. 4 is a side elevational view, in partial cross-section, of the device with canopy raised and in traditional IR warmer mode.

Referring to FIG. 4, it will be seen that patient support portion 5 includes a depending rectangular tubular portion 70 which slidably cooperates with an upwardly extending portion 71 of the base 7. A vertical drive 72 powered by motor 73 includes a piston portion 74 and a cylinder portion 75, the piston portion 74 for extending out of and retracting into the cylinder portion 75 and for raising and lowering the patient support portion 5.

Patient support surface 29 is essentially the top surface of an infant supporting mattress 80, either end of which is supported on weight scales or the like 81 for monitoring weight of an infant 6 supported thereon. An x-ray cartridge or the like 82 may be inserted underneath mattress 80 for x-raying of the infant 6. A storage area 83 underlying cartridge 82 provides additional storage and may be accessed by drawers 84.

An uninterrupted power supply 85 powers the fans and heaters of the air system during, for example, mobile transport of the device 1 when AC wall power is not available.

Canopy support arm 10 includes a piston portion 90 and a cylinder portion 91 powered by a motor 92 for raising and lowering of a horizontal portion 93. Horizontal portion 93 of canopy support arm 10 includes an infrared heater 94 on an underside thereof, and has mounted thereto the canopy 11. Canopy 11 includes two halves 11a and 11b which are hinged together and connected to the horizontal portion 93 of canopy support arm 10 at 100 and 101. The canopy halves 11a and 11b are rotatable through 90° upwardly to the configuration shown in FIG. 1, and downwardly through 90° to the configuration shown in FIG. 6. The pivoting canopy halves 11a and 11b thus provide additional access to infant 6 by care providers in addition to the access had by the raising and lowering of the canopy 11 by canopy support arm 10. Canopy halves 11a and 11b are preferably fabricated of transparent material, e.g., plexiglass. All or a portion of canopy 11, for example the head end portion of the canopy halves 11a, 11b as shown, includes a light reduction medium, for example a liquid crystal light shutter shown at 102, which allows selective darkening of the infant sleep surface.

Referring to FIG. 2, the head end 5b of the support portion 5 of the device 1 includes a raised portion 110 which includes a recessed area 111 therein. The recessed area 111 is designed as a shelf or storage area for storing various items, such as probes, probe covers, laryngoscopes, and resuscitation masks. This storage area 111 is preferably heated by placing a heating element or source as shown at 112 underneath the surface 113 of the storage area 111, thus heating the items stored thereon such that when those items come in contact with the infant 6 the infant is not startled or otherwise traumatized due to their otherwise cold nature. Raised area 110 further includes another storage area 115 in the rear vertically oriented face 116 of the raised structure 110 and is suitable for storage of probe wires, etc. Additionally, a speaker 117 is provided on face 116 of the structure 110 for directing suitable calming audible input into the infant's environment.

A combination controller and display 120 (FIGS. 1 and 6) is provided for controlling the motors 73 and 92 of the infant support 5 and canopy 11 drives, respectively, as well as blowers 31 and 40, heaters 52, 61 and 112, and light shutter 102, and for displaying patient data.

Figure 5:
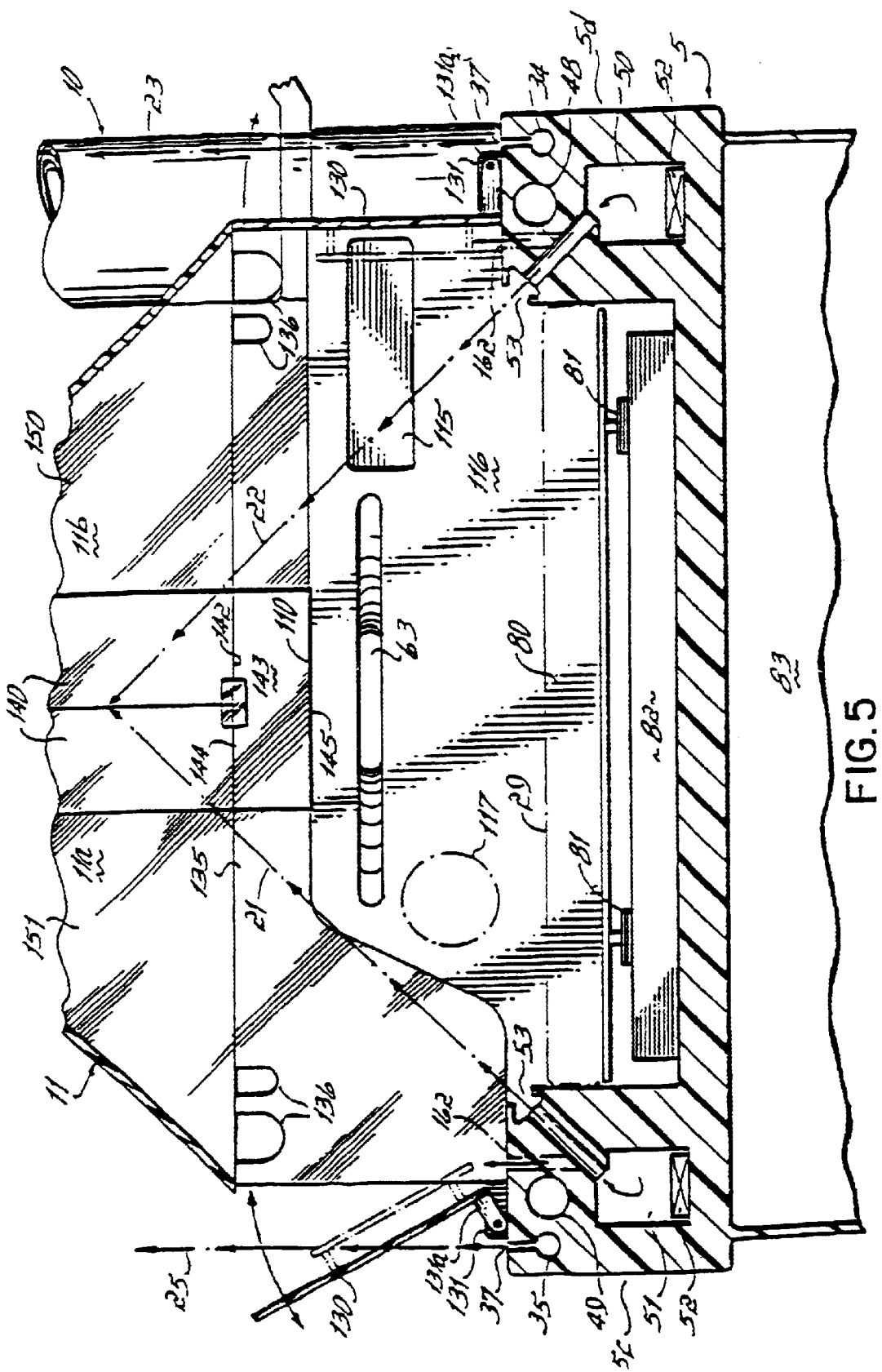
FIG. 5 is a view of the device taken along line 5—5 of FIG. 4 but with canopy lowered and in traditional incubator mode.
Figure 6:
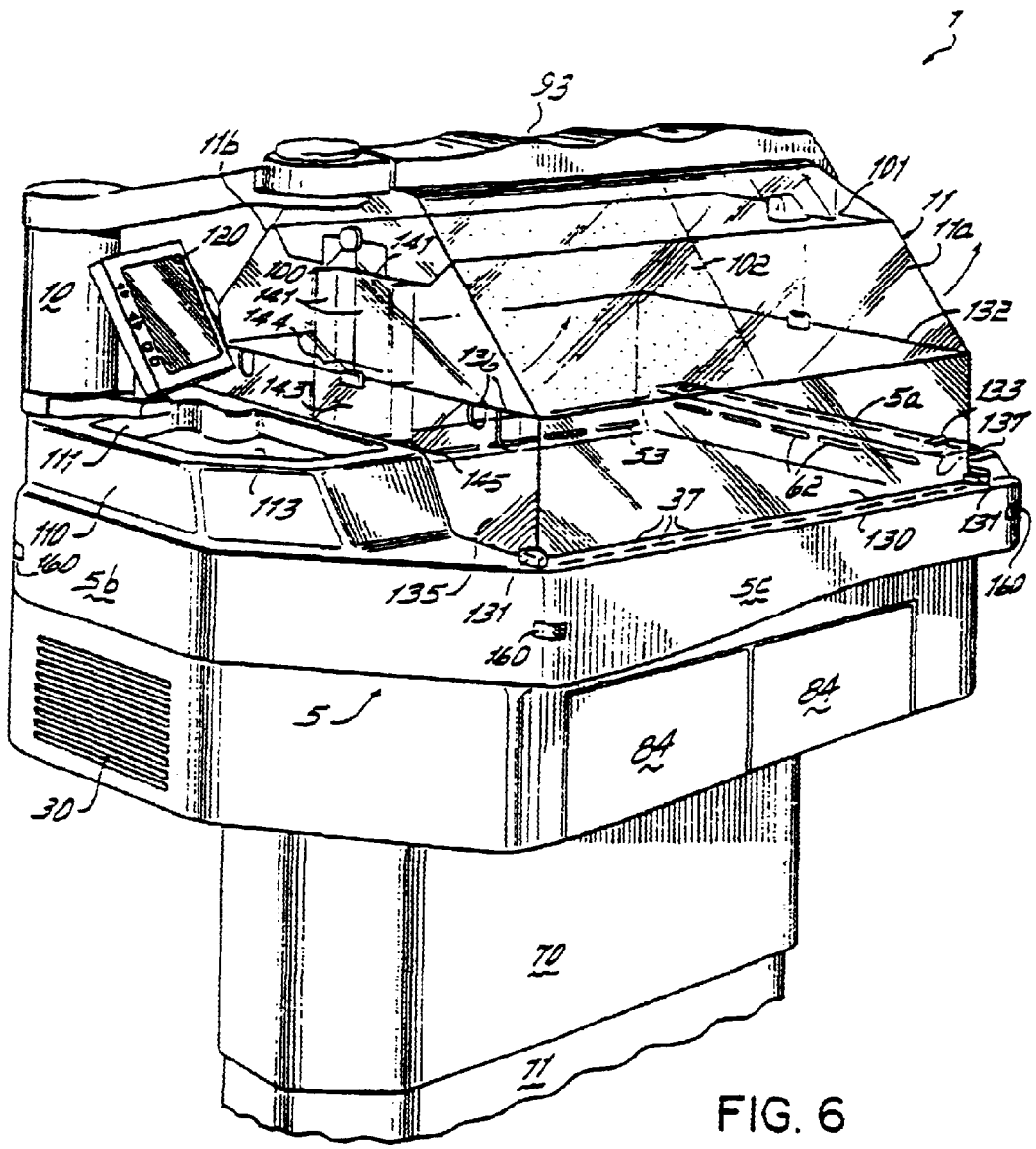
FIG. 6 is a perspective view of the device in traditional incubator mode.

Referring to FIGS. 1 and 6, transparent sideguards 130 fabricated of, e.g., plexiglass, are pivoted at either end by pivot joints 131 offset from respective sideguards 130 by offset arms 131a and may be pivoted downwardly (FIG. 5) to provide for increased access to infant 6. Similarly, a transparent footguard 132 likewise fabricated of, e.g., plexiglass, is similarly pivoted on its ends by pivot joints 133 offset from footguard 132 by offset arms (not shown) and may be pivoted downwardly for increased access. Due to their offset arms, sideguards 130 and footguard 132 provide unrestricted air flow from slots 37 for the air curtains 23, 24 and 25 whether the guards are up or down. At the head end of the support 5 an additional transparent panel 135 of, e.g., plexiglass, is removably secured there, as by slidably mounting within grooves (not shown), and is removable as well. Notches 136 in the upper edge of panel 135 near its corners provide for various life supporting lines to be run into the environment of the infant 6, as do notches 137 in the lateral edges of the foot end 5a of the support 5.

Referring to FIG. 6, it will be seen that when the canopy halves 11a, 11b are rotated downwardly, and when the canopy support arm 10 is driven downwardly by motor 92, the lower edges of the canopy support halves 11a, 11b engage with the upper edges of the guards 130, 130, 132, 135. The canopy 11 and infant support 5 thus form a substantial enclosure, essentially duplicating a traditional incubator.

To further enhance the efficiency of the thermal support device 1 of the present invention, and referring now to FIGS. 4–6, a convective air return slot 140 is incorporated into each of the head end panels 150, 151 of the canopy halves 11a and 11b. The convective air return slots are open at their upper ends 141. When the canopy halves are pivoted downwardly into the configuration shown in FIG. 6, the slots 140 in each of the panels 150, 151 come together to form a channel or passage having the above-described upper opening 141 and a lower opening 142. Head end panel 135 of support 5 likewise includes a similar convective return slot 143 having an upper opening 144 and a lower opening 145 forming a similar channel or passageway in the head end panel 135. When the canopy 11 is lowered onto the upper edges of the guards 130, 130, 132, 135 (FIG. 6), the lower opening 142 of passage 140 abuts the upper opening 144 of passage 143. Heated air from the air curtains 21 and 22 will be drawn into opening 141 and will pass downwardly through passages 140, 143 and into return or intake 63. Passages 140, 143 thus increase the efficiency of the convective air curtains 21 and 22 by recirculating heated air from those air curtains back through the pneumatic circuitry. An additional benefit of such a return is that it provides a means of cooling or reducing the heater 94 temperature mounted on the underside of canopy support arm 10 by convective cooling of the heater surface when the canopy is in a closed position.

Referring now to FIGS. 1, 2 and 6, a sensor 160 is mounted to each of the four corners of the infant supporting portion 5 of the device 1. The purpose of the sensors is to detect perturbations caused by the movement of care personnel and equipment around the device 1. When a sensor 160 is activated, it relays the disturbance information to the controller 120; the controller 120 then increases the speed of fan 31 hence increasing the velocity of the vertical air curtains 23, 24 and 25 to further increase the resistance of the heated air curtains 20, 21 and 22 to perturbations caused by the sensed physical disturbances. When the sensors 160 no longer sense the physical disturbance, the controller 120 would reduce the speed of the blower or fan 31 down to a lower nominal speed. Preferably the sensors would have a sensitivity detection adjustment range of approximately 3–6 ft. around the device 1.

To avoid heat loss from the infant thermal environment to the sideguards 130, a portion of the air curtains 21 and 22 is bled off to heat the sideguards 130. Referring to FIG. 5, slots 162 (phantom) are included within the portion 5 of the device 1 which communicate with the slots 53 which form the air curtains 21 and 22. Heated air exiting the slots 162 is directed upwardly along the interior faces of the side panels 130. Alternatively, the sideguards 130 could be of double wall construction (phantom), wherein the air exiting the slots 162 is directed between the inner and outer walls of the sideguards 130. Yet another method for warming the sideguards 130 would be to incorporate electrical strip heaters (not shown) within or on the sideguards 130.

Referring to FIG. 4, a position sensor 170 is incorporated within canopy support arm 10 to sense the position of the canopy 11 relative to the support 5. Controller 120 is operable, upon receiving input from sensor 170, to vary the speed of various ones of the fans and hence air curtains 20–25. As discussed previously, with the canopy raised, the air curtain 20 would have a velocity of up to approximately 0.1 meters per second, the air curtains 21 and 22 would have velocities up to approximately 0.5 meters per second and the air curtains 23–25 would have velocities up to approximately 1–2 meters per second. With the canopy 11 lowered atop the guards 130, 130, 132, 135 the sensor 170, sensing the lowered position of the canopy, would relay this information to the controller 120 which would adjust the speeds of the air curtains accordingly. With the canopy 11 in the lowered position, the need for the perturbation reducing curtains 23–25 diminishes or is obviated, and less heated air from the heated air curtains 20–22 is required to maintain warmth of the infant since the infant is substantially enclosed by canopy 11. The speed of the air curtain 20 would remain unchanged, whereas the speeds of the air curtains 21 and 22 would be reduced so as to range up to 0.1–0.2 meters per second, and the speeds of the air curtains 23–25 would be reduced so as to range up to 0.5 meters per second or less.

In use, the infant thermal support device of the present invention provides the convective heat transfer and humidification benefits of a traditional incubator, but allows totally unrestricted and complete access to an infant by the care provider. Upon placing the infant within the device, the sideguards can be installed in their upright configurations for safety. The hinged halves of the canopy can be pivoted upwardly, and the entire canopy can be raised upwardly, both offering complete access to the infant. The heated air curtains in effect provide a heated warm air canopy about the infant, while the upwardly oriented high speed air curtains reduce or prevent physical disturbances from creating perturbations in the three heated air curtains. Alternatively, the canopy halves can be pivoted downwardly, and the entire canopy lowered such that the canopy substantially encloses the infant support, as in traditional incubators. In this manner, the device can function as a traditional incubator.

Additionally, the device can function as a traditional radiant warmer by activating the infrared heater mounted in the canopy support arm. In this configuration, the canopy would be raised upwardly to its uppermost position. Should supplemental heating be required or desired, one or more of the heated air curtains can be activated, as well as the perturbation-reducing high speed vertical air curtains, to provide the appropriate amount of heat and humidity.

Those skilled in the art will readily recognize numerous adaptations of modifications which can be made to the infant thermal support device of the present invention which will result in an improved infant thermal support device, yet all of which will fall within the spirit and scope of the present invention as defined in the following claims. Accordingly, the invention is to be limited only by the following claims and their equivalents.

What is claimed is:

1. A combination infant warmer and incubator comprising:
   a base,
   a support for receiving an infant, the support being movable upwardly and downwardly on the base,
   side guards associated with the support, the side guards being movable between upright positions and lowered positions providing access to the infant,
   an assembly comprising a canopy and a radiant warmer,
   the assembly being movable upwardly and downwardly relative to the support between a lower position and an upper position,
   the canopy, in the lower position of the assembly, cooperating with the side guards, in the upright position, to form an incubator enclosure for receiving the infant, and
   the radiant warmer, in the upper position of the assembly, providing a radiant warmer for the infant on the surface.

2. The invention of claim 1, comprising a humidifier for providing moist air to the enclosure.

3. The invention of claim 1, comprising one or more weight scales coupled to the support for monitoring the weight of the infant.

4. The invention of claim 1, in which the support includes a head end and a foot end spaced-apart from the head end, the assembly comprising a canopy support at the head end, the canopy support being provided to raise and lower the canopy and radiant warmer relative to the support.

5. The invention of claim 1, further comprising a canopy support at one end of the support, the canopy and radiant warmer assembly being movable on the canopy support between its upper and lower positions.

6. The invention of claim 5, comprising a motor associated with the support for raising and lowering the assembly.

7. The invention of claim 1, wherein the side guards are pivotable in a direction away from the support to provide access to the infant.

8. An infant heater and warmer comprising:
   an infant support having a head end, a foot end, and opposite sides,
   a base coupled to the infant support, the infant support being movable upwardly and downwardly relative to the base to present the infant at selected heights,
   a canopy above the infant support,
   side and end guards associated with the infant support, the side guards being movable between upright positions and lowered open positions,
   the canopy being movable upwardly and downwardly relative to the support between a raised and a lowered position, the canopy and side and end guards cooperating to form an enclosure for the infant when the side guards are in the upright position and the canopy is in the lowered position, an air heater and blower, the air heater and blower and enclosure being configured to warm the infant in the enclosure, and a radiant heater to provide heat to the infant when the canopy is in the raised position, the radiant heater being movable with the canopy between its raised and lowered positions.

9. The invention of claim 8, wherein one of the end guards is a foot end guard that is pivotable from an upright position to a lowered open position and pivoting the side and end guards to their lowered open positions provides increased access to the infant.

10. The invention of claim 8, further comprising a humidifier, the humidifier, air heater and blower and enclosure being configured to provide moist warm air for the infant.

11. The invention of claim 8, further comprising one or more weight scales positioned to support a mattress of the infant support in order to monitor the weight of the infant on the mattress.

12. The invention of claim 8, further including a support coupled at the head end of the infant support, the canopy and radiant heater being movable on the support upwardly and downwardly relative to the infant support.

13. The invention of claim 8, wherein a controller and display assembly is provided for controlling the movement and is positioned at the head end of the support.

14. An infant thermal support comprising:

a base portion, an infant support coupled to the base portion and having a head end, a foot end, and opposite sides, and opposite side guards, a head wall, and an end wall, the side guards and head and end walls having upright positions to protect the infant on the support, at least the side guards being movable downwardly to provide access to the infant, the infant support being movable upwardly and downwardly relative to the base portion to present the infant at selected heights, and a canopy positioned above the infant support and vertically movable relative to the infant support between a raised position wherein the canopy is spaced-apart from the side guards, end wall, and head wall and a lowered position wherein the canopy cooperates with the side guards, end wall, and head wall to form an incubator enclosure, and an air heater, humidifier, and blower configured to cooperate with the enclosure to provide a warm, moist environment for the infant.

15. The infant thermal support of claim 14, further including a support coupled to the canopy and the head end of the infant support to support the canopy for movement between its positions.

16. The infant thermal support of claim 15, further including a first motor for raising and lowering the canopy relative to the infant support and a second motor for rasing and lowering the infant support relative to the base portion.

17. The infant thermal support of claim 14, wherein the infant support further includes weight scales.

18. The infant thermal support of claim 14, further including a radiant warmer coupled to the canopy for movement therewith, the radiant warmer being configured to warm the infant on the support when the canopy is in its raised position.

19. The infant thermal support of claim 14, wherein the side guards and the end wall of the infant support portion are pivotable downwardly in a direction away from the support surface to provide access to the infant.

20. The infant thermal support of claim 16, further including a controller and display combination positioned at the head end of the infant support for controlling the first and second motors.

21. An infant warmer comprising:

a support for receiving an infant, a canopy and radiant warmer assembly supported above the support and movable between a raised position and a lowered position relative to the support, side guards surrounding the support and position to extend vertically upwardly from the support, the canopy and radiant warmer assembly cooperating with the side guards to form an enclosure for the infant when the canopy and radiant warmer assembly is in its lowered position.

22. The infant warmer of claim 21, further including a heater and blower for heating the enclosure when the canopy and radiant warmer assembly is in its lowered position.

23. The infant warmer of claim 21, further including a humidifier for providing moist air to the enclosure.

24. The infant warmer of claim 21, further including a canopy support for supporting the canopy and radiant warmer assembly above the support, the canopy support being positioned at a head end of the support.

25. The infant warmer of claim 21, further including a base coupled to the support, the support being movable upwardly and downwardly relative to the base.

26. The infant warmer of claim 21, wherein the side guards are pivotable relative to the support in a direction away from the support surface in order to provide access to the infant on the support.

27. The infant warmer of claim 21, further including a weight scale coupled to the support and provided for monitoring the weight of the infant.

28. An infant thermal support device comprising a support defining edges adjacent the perimeter of the support surface, side guards adjacent the edges of the support, and a radiant warmer assembly configured to warm the infant on the support when the radiant warmer assembly is activated, the radiant warmer assembly being movable between a first position spaced apart from the support and a second position between the support and the first position, the radiant warmer assembly cooperating with the side guards when the radiant warmer assembly is in the second position to form an incubator enclosure receiving the infant, the radiant warmer assembly in its upper position providing a radiant warmer for the infant.

29. The infant thermal support device of claim 28, wherein the side guards are movable between a first position having top edges of the side guards above the support and an out-of-the-way position away from the first position, the side guards cooperating with the radiant warmer assembly to form the incubator enclosure when the side guards are in the first position of the side guards and the radiant warmer assembly is in the second position of the radiant warmer assembly, the side guards cooperating with the radiant warmer assembly to permit access to the support when the side guards are in the out-of-the-way position of the side guards and the radiant warmer assembly is in the first position of the radiant warmer assembly.

* * * * *